United States Patent [19]

Eilingsfeld et al.

[11] 4,407,810

[45] Oct. 4, 1983

[54] THIAZOL-2-YL-OXAMIC ACID DERIVATIVES, AND THERAPEUTIC AGENTS CONTAINING THESE COMPOUNDS

[75] Inventors: Heinz Eilingsfeld, Frankenthal; Peter Neumann, Wiesloch; Guenther Seybold, Neuhofen; Dieter Lenke, Ludwigshafen; Ludwig Friedrich, Bruehl, all of Fed. Rep. of Germany

[73] Assignee: BASF Aktiengesellschaft, Fed. Rep. of Germany

[21] Appl. No.: 282,661

[22] Filed: Jul. 13, 1981

[30] Foreign Application Priority Data

Jul. 19, 1980 [DE] Fed. Rep. of Germany ....... 3027527

[51] Int. Cl.$^3$ .................... C07D 277/20; A61K 43/78
[52] U.S. Cl. .................................. 424/270; 548/194; 548/195
[58] Field of Search ............... 548/190, 194, 195, 196; 424/270

[56] References Cited

U.S. PATENT DOCUMENTS

| | | | |
|---|---|---|---|
| 3,966,965 | 6/1976 | Sellstedt et al. | 424/309 |
| 4,115,140 | 4/1979 | Hall et al. | 424/270 |
| 4,238,496 | 12/1980 | Hess et al. | 424/270 |
| 4,246,271 | 1/1981 | Cousse et al. | 424/270 |

FOREIGN PATENT DOCUMENTS

| | | |
|---|---|---|
| 6368 | 1/1980 | European Pat. Off. . |
| 2132431 | 1/1973 | Fed. Rep. of Germany . |
| 2144683 | 3/1973 | Fed. Rep. of Germany . |
| 2413966 | 9/1974 | Fed. Rep. of Germany . |
| 2656468 | 6/1978 | Fed. Rep. of Germany . |
| 2751441 | 6/1978 | Fed. Rep. of Germany . |
| 2828091 | 1/1980 | Fed. Rep. of Germany . |
| 460017 | 3/1965 | Switzerland . |
| 1538822 | 1/1979 | United Kingdom . |

*Primary Examiner*—Nicholas S. Rizzo
*Attorney, Agent, or Firm*—Keil & Witherspoon

[57] ABSTRACT

Novel 2-substituted thiazol-2-yl-oxamic acid esters, processes for their preparation, and therapeutic agents which contain these compounds and are useful in the treatment of allergic disorders.

8 Claims, No Drawings

THIAZOL-2-YL-OXAMIC ACID DERIVATIVES, AND THERAPEUTIC AGENTS CONTAINING THESE COMPOUNDS

The present invention relates to novel 4-substituted thiazol-2-yl-oxamic acid esters, processes for their preparation, and therapeutic agents which contain these compounds and are useful in the treatment of allergic disorders.

A range of derivatives of oxamic acid and their esters, stated to be useful in counteracting or suppressing allergic reactions, has been disclosed; for example aryl and hetaryl derivatives are disclosed in German Laid-Open Application DOS No. 2,413,966, thiazole derivatives in German Laid-Open Application DOS No. 2,828,091 and European Published Application No. 0,006,368 and benzothiazole derivatives in German Laid-Open Applications DOS Nos. 2,751,441 and 2,656,486. However, the effects of these compounds are not always satisfactory.

We have found that compounds of the general formula I

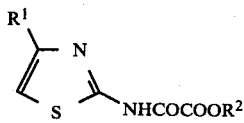

where $R^1$ is phenyl, biphenylyl or 4-cyclohexylphenyl, or is phenyl which is monosubstituted or disubstituted by halogen, alkyl of 1 to 4 carbon atoms, alkoxy of 1 to 4 carbon atoms, acetoxy, benzyloxy, phenoxy, methylthio, dialkylamino (where alkyl is of 1 or 2 carbon atoms), nitro, cyano, carboalkoxy (where alkyl is of 1 to 4 carbon atoms) or carboxamido, or is phenyl which is trisubstituted by methyl, ethyl, hydroxy, methoxy, ethoxy or acetoxy, or is a radical of the formula

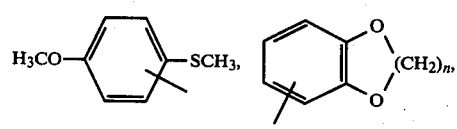

where n can be 1 or 2,

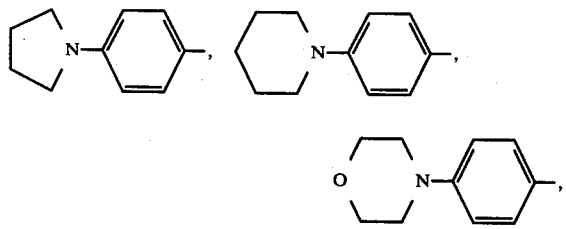

or naphthyl which can be substituted by methoxy, or is a radical of the formula

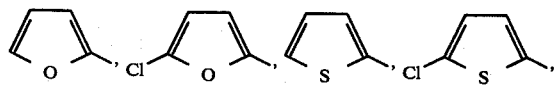

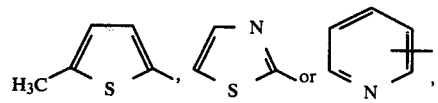

and $R^2$ is phenyl which can be substituted by alkyl of 1 to 4 carbon atoms, or is cyclopentyl or cyclohexyl which can be substituted by from one to four methyl groups or by an alkyl radical of 2 to 4 carbon atoms or by one methyl group and one alkyl radical of 2 to 4 carbon atoms, or is phenylalkyl of 8 or 9 carbon atoms, which can be substituted in the phenyl ring by one, two or three methyl or methoxy groups, or is a radical of the formula

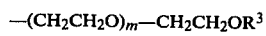

$-(CH_2CH_2O)_m-CH_2CH_2OR^3$ where m is an integer from 0 to 9 and $R^3$ is hydrogen, phenyl, alkyl of 1 to 4 carbon atoms or alkylcarbonyl (where alkyl is of 1 to 4 carbon atoms), or $R^2$ is a radical of the formula

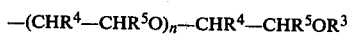

$-(CHR^4-CHR^5O)_n-CHR^4-CHR^5OR^3$ where $R^4$ and $R^5$ are each hydrogen or methyl and n and $R^3$ have the above meanings, or $R^2$ is a radical of the formula

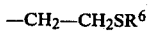

$-CH_2-CH_2SR^6$ where $R^6$ is alkyl of 1 to 4 carbon atoms, or $R^2$ is a radical of the formula

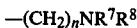

$-(CH_2)_nNR^7R^8$ where n can be 2 or 3 and $R^7$ and $R^8$ are each alkyl of 1 to 4 carbon atoms, or $-NR^7R^8$ is pyrrolidyl, piperidyl, morpholinyl or (N'-methyl)-piperazinyl, or $R^2$ is a radical of the formula

$CH_2CH_2OCH_2CH_2NR^7R^8$ where $R^7$ and $R^8$ have the above meanings, exhibit valuable pharmacological properties, especially as anti-allergics.

Specific examples of the radicals $R^1$ are phenyl, 2-, 3- and 4-methylphenyl, 2-, 3- and 4-hydroxyphenyl, 2-, 3- and 4-methoxyphenyl, 2-, 3- and 4-ethoxyphenyl, 2,4-dihydroxyphenyl, 3,4-dihydroxyphenyl, 2,5-dihydroxyphenyl, 2,4-dimethoxyphenyl, 2,4-diethoxyphenyl, 3,4-dimethoxyphenyl, 3,4-diethoxyphenyl, 2,5-dimethoxyphenyl, 2,5-diethoxyphenyl, 3,5-dimethoxyphenyl, 2-hydroxy-3-methoxyphenyl, 2-methyl-4-hydroxyphenyl, 3-methyl-4-hydroxyphenyl, 2-hydroxy-5-methylphenyl, 2-hydroxy-4,6-dimethylphenyl, 2-methyl-4-methoxyphenyl, 3-methyl-4-methoxyphenyl, 2-methoxy-5-methylphenyl, 2,3,4-trimethoxyphenyl, 3,4,5-trimethoxyphenyl, 2,4,5-trimethoxyphenyl, 2,4,6-trimethoxyphenyl, 4-hydroxy-3,5-dimethoxyphenyl, 2-hydroxy-4,6-dimethoxyphenyl, 3,4-methylenedioxyphenyl, 3,4-ethylenedioxyphenyl, 4-dimethylaminophenyl, 4-diethylaminophenyl, 2-, 3- and 4-pyridyl and 2-thienyl.

Amongst these, preferred radicals $R^1$ are phenyl which is unsubstituted, or is monosubstituted or disubstituted by hydroxyl or monosubstituted, disubstituted or trisubstituted by methoxy or ethoxy or monosubstituted by methylenedioxy or ethylenedioxy, eg. phenyl, 2-, 3- and 4-hydroxyphenyl, 2-, 3- and 4-methoxyphenyl, 2,4-dihydroxyphenyl-3,4-dihydroxyphenyl, 2,4-dimethoxyphenyl, 3,4-dimethoxyphenyl, 2,5-dimethoxyphenyl, 3,5-dimethoxyphenyl, 2,4-diethoxyphenyl, 3,4-diethoxyphenyl, 3,4,5-trimethoxyphenyl, 3,4-methylenedioxyphenyl and 3,4-ethylenedioxyphenyl.

Specific examples of radicals $R^2$ are cyclopentyl and cyclohexyl, which can be substituted by from 1 to 4 methyl groups or by an alkyl radical of 2 to 4 carbon atoms or by one methyl group and one alkyl radical of 2 to 4 carbon atoms, a radical of the formula $-(CH_2CH_2O)_m-CH_2CH_2OR^3$, where m is an integer from 0 to 9 and $R^3$ is hydrogen, alkyl of 1 to 4 carbon atoms or alkylcarbonyl (where alkyl is of 1 to 4 carbon atoms), a radical of the formula $-(CHR^4-CHR^5O)_n-CHR^4-CHR^5OR^3$, where $R^4$ and $R^5$ are each hydrogen or methyl and n and $R^3$ have the above meanings, and a radical of the formula $-CH_2-CH_2-SR^6$, where $R^6$ is alkyl of 1 to 4 carbon atoms. Preferred radicals $R^2$ are radicals of the formula $-(CH_2CH_2O)_m-CH_2CH_2OR^3$, where m is an integer from 0 to 3 and $R^3$ is hydrogen or alkyl of 1 to 4 carbon atoms, and radicals of the formula $-(CHR^4-CHR^5O)_n-CHR^4-CHR^5OR^3$, where $R^4$ and $R^5$ are each hydrogen or methyl, n is an integer from 0 to 3 and $R^3$ is hydrogen or alkyl of 1 to 4 carbon atoms. Such preferred radicals are derived, for example, from the monomethyl, monoethyl or monobutyl ethers of ethylene glycol, diethylene glycol, triethylene glycol, tetraethylene glycol or propylene glycol.

Particularly preferred compounds of the formula I are those where $R^1$ is phenyl, which is unsubstituted or substituted by methoxy, and $R^2$ is a radical of the formula $-(CH_2CH_2O)_m-CH_2CH_2OR^3$, where m is 0 or 1 and $R^3$ is alkyl of 1 to 4 carbon atoms.

Specific examples of compounds according to the invention are the esters formed from ethylene glycol, diethylene glycol, triethylene glycol, tetraethylene glycol, pentaethylene glycol, hexaethylene glycol, heptaethylene glycol, octaethylene glycol, nonaethylene glycol, decaethylene glycol, propylene glycol, dipropylene glycol, tripropylene glycol, tetrapropylene glycol, pentapropylene glycol, hexapropylene glycol, heptapropylene glycol, octapropylene glycol, nonapropylene glycol, decapropylene glycol, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, triethylene glycol monobutyl ether, tetraethylene glycol monomethyl ether, tetraethylene glycol monoethyl ether, tetraethylene glycol monobutyl ether, pentaethylene glycol monomethyl ether, pentaethylene glycol monoethyl ether, pentaethylene glycol monobutyl ether, hexaethylene glycol monomethyl ether, hexaethylene glycol monoethyl ether, hexaethylene glycol monobutyl ether, heptaethylene glycol monomethyl ether, heptaethylene glycol monoethyl ether, heptaethylene glycol monobutyl ether, octaethylene glycol monomethyl ether, octaethylene glycol monoethyl ether, octaethylene glycol monobutyl ether, nonaethylene glycol monomethyl ether, nonaethylene glycol monoethyl ether, nonaethylene glycol monobutyl ether, decaethylene glycol monomethyl ether, decaethylene glycol monoethyl ether, decaethylene glycol monobutyl ether, propylene glycol monomethyl ether, propylene glycol monoethyl ether, propylene glycol monobutyl ether, dipropylene glycol monomethyl ether, dipropylene glycol monoethyl ether, dipropylene glycol monobutyl ether, tripropylene glycol monomethyl ether, tripropylene glycol monoethyl ether, tripropylene glycol monobutyl ether, tetrapropylene glycol monomethyl ether, tetrapropylene glycol monoethyl ether, tetrapropylene glycol monobutyl ether, pentapropylene glycol monomethyl ether, pentapropylene glycol monoethyl ether, pentapropylene glycol monobutyl ether, hexapropylene glycol monomethyl ether, hexapropylene glycol monoethyl ether, hexapropylene glycol monobutyl ether, heptapropylene glycol monomethyl ether, heptapropylene glycol monoethyl ether, heptapropylene glycol monobutyl ether, octapropylene glycol monomethyl ether, octapropylene glycol monoethyl ether, octapropylene glycol monobutyl ether, nonapropylene glycol monomethyl ether, nonapropylene glycol monoethyl ether, nonapropylene glycol monobutyl ether, decapropylene glycol monomethyl ether, decapropylene glycol monoethyl ether, decapropylene glycol monopropyl ether and decapropylene glycol monobutyl ether with N-(4-phenyl-thiazol-2-yl)-oxamic acid, N-[4-(2-hydroxyphenyl)-thiazol-2-yl]-oxamic acid, N-[4-(3-hydroxyphenyl)-thiazol-2-yl]-oxamic acid, N-[4-(4-hydroxyphenyl)-thiazol-2-yl]-oxamic acid, N-[4-(2-methoxyphenyl)-thiazol-2-yl]-oxamic acid, N-[4-(3-methoxyphenyl)-thiazol-2-yl]-oxamic acid, N-[4-(4-methoxyphenyl)-thiazol-2-yl]-oxamic acid, N-[4-(2-ethoxyphenyl)-thiazol-2-yl]-oxamic acid, N-[4-(3-ethoxyphenyl)-thiazol-2-yl]-oxamic acid, N-[4-(4-ethoxyphenyl)-thiazol-2-yl]-oxamic acid, N-[4-(2,4-dihydroxyphenyl)-thiazol-2-yl]-oxamic acid, N-[4-(3,4-dihydroxyphenyl)-thiazol-2-yl]-oxamic acid, N-[4-(2,4-dimethoxyphenyl)-thiazol-2-yl]-oxamic acid, N-[4-(3,4-dimethoxyphenyl)-thiazol-2-yl]-oxamic acid, N-[4-(2,5-dimethoxyphenyl)-thiazol-2-yl]-oxamic acid, N-[4-(3,5-dimethoxyphenyl)-thiazol-2-yl]-oxamic acid, N-[4-(2,4-diethoxyphenyl)-thiazol-2-yl]-oxamic acid, N-[4-(3,4-diethoxyphenyl)-thiazol-2-yl]-oxamic acid, N-[4-(2,5-diethoxyphenyl)-thiazol-2-yl]-oxamic acid, N-[4-(2-hydroxy-4-methoxyphenyl)-thiazol-2-yl]-oxamic acid and N-[4-(3-methoxy-4-hydroxyphenyl)-thiazol-2-yl]-oxamic acid.

The compounds according to the invention, of the formula I, are prepared by a process wherein a 2-aminothiazole of the formula II

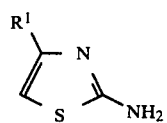

where $R^1$ has the meanings given for formula I, is reacted with an oxalic acid ester halide of the formula III

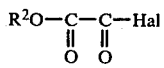

where $R^2$ has the meanings given for formula I and Hal is halogen, preferably chlorine, in a conventional manner, advantageously in a solvent and in the presence of an acid acceptor.

Examples of suitable solvents are methylene chloride, chloroform, carbon tetrachloride, 1,2-dichloroethane, 1,1,1-trichloroethane, ethyl acetate, dimethylformamide, dimethylacetamide, N-methylpyrrolidone, tetrahydrothiophene dioxide, hexamethylphosphorotriamide, tetrahydrofuran, dioxane or mixtures of these. Examples of acid acceptors are triethylamine, tributylamine and pyridine. The reaction between the aminothiazole II with the oxalyl halide III is preferably carried out at a relatively low temperature, usually at from 0° C. to 30° C. In place of the free aminothiazoles, the hydrochlorides can be used if an additional equivalent of base is employed.

Oxamic acid esters of the formula I, where $R^2$ is, for example, unsubstituted or substituted cyclopentyl or cyclohexyl, can also be obtained from a 2-aminothiazole of the formula II and the corresponding oxalic acid diester. The reaction takes place direct, in an undiluted form, or with addition of a solvent, such as xylene, at from room temperature to the reflux temperature of the reaction mixture.

Oxamic acid esters of the formula I can also be obtained by conventional processes described, for example, in Swiss Pat. No. 512,257, by trans-esterifying the corresponding lower alkyl oxamate with an alcohol of the formula $R^2OH$, where $R^2$ has the meanings given for formula I.

The oxamic acid esters according to the invention can also be prepared in a conventional manner from the free oxamic acids of the formula I, ie. if $R^2$ is hydrogen, by converting the acid to the oxamic acid chloride and then esterifying with an alcohol of the formula $R^2OH$, where $R^2$ has the meanings given for formula I, in the presence of an acid acceptor, such as triethylamine.

The oxamic acids are obtained from the esters of the formula I, especially lower alkyl esters, by conventional hydrolysis.

The esterification of the oxamic acids can also be carried out in the presence of an acidic catalyst or of a carbodiimide, as described in Chem. Ber. 100 (1967), 16 and in Acta Chem. Scand. B 33 (1979), 410. The esterification of the free oxamic acid can also be effected by means of a dimethylformamide-acetal, using the imidazolide method ([Chem. Ber. 95 (1962), 1284] or by the method described in Bull. Chem. Soc. Japan 50 (1977), 1863).

Some of the 4-substituted 2-aminothiazoles of the general formula II

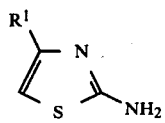

II used as starting materials are novel; they can be prepared by the cyclization methods described in the literature (for example "The Chemistry of Heterocyclic Compounds, Thiazoles and its Derivatives", edited by J. V. Metzger, Volume 1, page 213 et seq.).

The compounds according to the invention exhibit anti-allergic properties, and because of these can be used as valuable drugs in the treatment of allergic disorders of the respiratory tract, the gastro-intestinal tract and the skin, for example the treatment of allergic asthma, allergic rhinitis or food allergies. Compared to the known anti-allergic Cromolyne, the novel compounds, tested in animal experiments in passive cutaneous anaphylaxis of rats, prove to have the advantage of being orally effective and, additionally, having a substantially longer period of action.

The anti-allergic action was tested on rats, using the passive cutaneous anaphylaxis (PCA) model.

Narcotized male rats (100-140 g) are sensitized by intradermal injection (into the shaved dorsal skin) of 0.1 ml of an ovalbumin antiserum. After a sensitization period of about 48 hours, the treatment (intraperitoneal or oral administration) is carried out with various dosages (10 animals/dose) of the test substances. 15-20 minutes after treatment, an antigen/Evans blue mixture (10 mg/kg of ovalbumin in 2% strength Evans blue solution) is intravenously injected into the test animals. 30 minutes later, the animals are sacrificed, the dorsal skin is removed and the diameter of the circular blue coloration is measured on the inner surface. The size of the color patches of untreated control animals can be standardized. Anti-allergic substances reduce the diameter of the color patch by an amount dependent on the dose. The ED 50% is quoted as the dose which reduces the diameter of the color patch by 50% relative to that of non-medicated control animals.

In addition to the anti-allergic action, the acute toxicity was determined for intraperitoneal administration, using groups of 2 NMRI mice, each weighing 20-26 g, and for oral administration, using groups of 2 Sprague-Dawley rats, each weighing 120-150 g. The LD 50 was determined on groups of 10 NMRI mice, each weighing 20-26 g, after intraperitoneal administration. The post-observation period was 14 days.

The compounds according to the invention are highly active as anti-allergics. Table 1 shows that these substances, after oral administration, are from 3.87 times (Example 7) to 227 times (Example 9) more active than the Comparative Compound $V_1$ (ethyl N-(4-phenylthiazol-2-yl)-oxamate, Example 1 of European Published Patent No. 0,006,368). With this test method, the commercial compound Cromolyne is inactive at up to 100 mg/kg administered orally.

TABLE 1

| | Anti-allergic action and acute toxicity | | | |
|---|---|---|---|---|
| | Inhibition of PCA in rats (oral) | | LD 50 mg/kg | |
| Example No. | ED 50% mg/kg | R.A. | Mice intra-peritoneal | Rats oral |
| 7 | 2.24 | 3.87 | 655 | >2,150 |
| 9 | 0.0382 | 227 | 956 | >2,150 |
| 11 | 2.16 | 4.01 | 705 | >2,150 |
| 14 | 0.619 | 14.0 | about 1,000 | |
| $V_1$ | 8.67 | 1 | about 681 | >2,150 |
| Cromolyne | 100 | — | — | >2,150 |

(1) relative activity

Because of the greater activity, the quotient of the toxic dose of the effective dose is substantially greater.

For therapeutic use, individual doses of 0.1-100 mg are employed.

Accordingly, the present invention also relates to therapeutic agents or formulations which, in addition to conventional carriers and diluents, contain a compound of the formula I as the active compound, and to the use of the novel compounds in the treatment of allergic disorders.

The preferred formulations are those suitable for oral administration. They include, for example, tablets, film tablets, dragees, capsules, pills, powders, solutions, suspensions or depot forms. Inhalation formulations and parenteral formulations, such as injection solutions, may also be used.

The pharmaceutical, solid or liquid, use forms are prepared in a conventional manner. To do so, the active compounds can be compounded with the conventional pharmaceutical auxiliaries, such as talc, gum arabic, sucrose, lactose, grain starch or corn starch, potato flour, magnesium stearate, alginates, gum tragacanth, carraghenates, polyvinyl alcohol, polyvinylpyrrolidone, aqueous or non-aqueous vehicles, wetting agents, dispersants, emulsifiers and/or preservatives (cf. L. G. Goodman and A. Gilman, The Pharmacological Basis of Therapeutics).

The Examples which follow illustrate the invention without implying any limitation.

EXAMPLE 1

Cyclohexyl N-(4-phenyl-thiazol-2-yl)-oxamate 8.8 g of 2-amino-4-phenylthiazole are dissolved in a mixture of 40 ml of dry dimethylformamide and 6.1 g of triethylamine. 11.4 g of cyclohexyl-oxalyl chloride are added dropwise, whilst cooling with ice water, at a rate such that the temperature does not rise above 15° C. The mixture is then stirred for one hour at from 0° to 10° C. and thereafter for about 20 hours (overnight) at room temperature. It is poured into ice water, the batch is stirred for about 15 minutes, and the precipitate formed is filtered off. After recrystallization from ethanol, 11.3 g of the compound of the formula I, where $R^1=C_6H_5$ and $R^2=C_6H_{11}$, of melting point 160°–161° C., are obtained.

|            | C     | H    | O     | N    | S    |
|------------|-------|------|-------|------|------|
| calculated | 61.80 | 5.49 | 14.53 | 8.48 | 9.70 |
| found      | 61.80 | 5.5  | 14.4  | 8.4  | 9.6  |

EXAMPLE 2

Menthyl N-(4-phenyl-thiazol-2-yl)-oxamate

Starting from 14.6 g of menthyl-oxalyl chloride and using a method similar to Example 1, crystallization of the product from isobutanol gives 7.0 g of the compound of the formula I, with $R^1=C_6H_5$ and

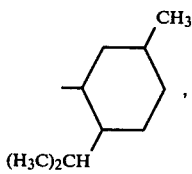

of melting point 98°–100° C.

| | $C_{21}H_{26}O_3N_2S$ (387) | | | | |
|------------|-------|------|-------|------|------|
|            | C     | H    | O     | N    | S    |
| calculated | 65.26 | 6.78 | 12.42 | 7.25 | 8.30 |
| found      | 65.4  | 6.8  | 12.6  | 7.0  | 8.3  |

EXAMPLE 3

2-Phenylethyl N-(4-phenyl-thiazol-2-yl)-oxamate

Using a method similar to Example 1, but with 12.6 g of 2-phenylethyl-oxalyl chloride in place of 11.4 g of cyclohexyl-oxalyl chloride, crystallization of the product from ethanol gives 7.1 g of the compound of the formula I, with $R^1=C_6H_5$ and $R^2=CH_2-CH_2-C_6H_5$, of melting point 152°–153° C.

| | $C_{19}H_{16}O_3N_2S$ (352) | | | | |
|------------|-------|------|-------|------|------|
|            | C     | H    | O     | N    | S    |
| calculated | 64.76 | 4.58 | 13.62 | 7.95 | 9.10 |
| found      | 64.8  | 4.7  | 13.6  | 8.1  | 9.1  |

EXAMPLE 4

2-Phenylethyl N-[4-(4-methoxyphenyl)-thiazol-2-yl]-oxamate

Using a method similar to Example 1, 10.3 g of 4-(4-methoxyphenyl)-2-aminothiazole and 12.8 g of 2-phenylthyl-oxalyl chloride give, after crystallization of the product from propanol, 14.0 g of the compound of the formula I, with $R^1=4\text{-}OCH_3-C_6H_4$ and $R^2=CH_2CH_2-C_6H_5$, of melting point 165°–167° C.

| | $C_{20}H_{18}O_4N_2S$ (382) | | | | |
|------------|-------|------|-------|------|------|
|            | C     | H    | O     | N    | S    |
| calculated | 62.81 | 4.74 | 16.73 | 7.32 | 8.38 |
| found      | 63.0  | 4.8  | 16.6  | 7.3  | 8.4  |

EXAMPLE 5

2-Phenylpropyl N-(4-phenyl-thiazol-2-yl)-oxamate

Starting from 13.6 g of 2-phenylpropyl-oxalyl chloride and using a method similar to Example 1, crystallization of the product from propanol gives 13.7 g of the compound of the formula I, with $R^1=C_6H_5$ and $R^2=CH_2CH(CH_3)-C_6H_5$, of melting point 140°–141° C.

| | $C_{20}H_{18}O_3N_2S$ (366) | | | | |
|------------|-------|------|-------|------|------|
|            | C     | H    | O     | N    | S    |
| calculated | 65.56 | 4.95 | 13.10 | 7.64 | 8.75 |
| found      | 65.6  | 4.9  | 12.9  | 7.6  | 9.2  |

EXAMPLE 6

2-Phenylpropyl N-[4-(4-methoxyphenyl)-thiazol-2-yl]-oxamate

Using a method similar to Example 1, 10.3 g of 4-(4-methoxyphenyl)-2-aminothiazole and 13.6 g of 2-phenylpropyl-oxalyl chloride give, after crystallization of the product from ethanol, 11.6 g of the compound of the formula I, with $R^1=4-OCH_3C_6H_4$ and $R^2=CH_2-CH(CH_3)-C_6H_5$, of melting point 150°–152° C.

| | $C_{21}H_{20}O_4N_2S$ (396) | | | | |
|------------|-------|------|-------|------|------|
|            | C     | H    | O     | N    | S    |
| calculated | 63.62 | 5.08 | 16.14 | 7.07 | 8.09 |
| found      | 63.6  | 5.1  | 16.1  | 7.1  | 8.2  |

EXAMPLE 7

2-Methoxyethyl N-(4-phenyl-thiazol-2-yl)-oxamate 6.2 g of N-(4-phenyl-thiazol-2-yl)-oxamic acid (prepared from the ethyl ester by hydrolyzing with aqueous potassium acetate and liberating the acid with dilute hydrochloric acid), in 25 ml of dry toluene, are heated with 20 ml of oxalyl chloride for 2 hours at 60° C. After distilling off the excess oxalyl chloride under reduced pressure, a solution of 5 ml of ethylene glycol monomethyl ether, 3.5 ml of triethylamine and 20 ml of toluene is added dropwise. The mixture is stirred for a further 3 hours at room temperature and is then left to stand overnight. The precipitate is filtered off, washed with methanol and water and recrystallized from ethanol. 3.7 g of the compound of the formula I, with $R^1 = C_6H_5$ and $R^2 = CH_2CH_2OCH_3$, of melting point 118°–120° C., are obtained.

| $C_{14}H_{14}O_4N_2S$ | | | | |
|---|---|---|---|---|
| C | H | O | N | S |
| calculated 54.89 | 4.61 | 20.89 | 9.14 | 10.47 |
| found 55.0 | 4.5 | 20.8 | 9.2 | 10.4 |

EXAMPLE 8

1-Methyl-2-methoxyethyl N-(4-phenyl-thiazol-2-yl)-oxamate

A solution of 1-methyl-2-methoxyethyl-oxalyl chloride in 15 ml of dry methylene chloride is added dropwise, at about 10° C., to a solution of 8.8 g of 4-phenyl-2-aminothiazole in 125 ml of dry methylene chloride and 8.05 ml of dry pyridine. The mixture is stirred for 1 hour at 10° C. and a further hour at room temperature, and the precipitate formed is then filtered off. The filtrate is concentrated under reduced pressure and the residue is digested with dilute hydrochloric acid. The product is filtered off, washed with water and dried. After crystallization from ethanol, 8.0 g of the compound of the formula I, with $R^1 = C_6H_5$ and $R^2 = CH(CH_3)CH_2CH_2OCH_3$, of melting point 152°–155° C. are obtained.

| $C_{15}H_{16}O_4N_2S$ (320) | | | | |
|---|---|---|---|---|
| C | H | O | N | S |
| calculated 56.24 | 5.03 | 19.98 | 8.74 | 10.01 |
| found 56.0 | 5.2 | 19.1 | 8.9 | 9.6 |

EXAMPLE 9

2-Ethoxyethyl N-(4-phenyl-thiazol-2-yl)-oxamate

Using a method similar to Example 7, 6.2 g of N-(4-phenyl-2-aminothiazolyl)-oxamic acid and 5.6 g of ethylene glycol monoethyl ether give, after crystallization of the product from ethanol, 3.3 g of the compound of the formula I, with $R^1 = C_6H_5$ and $R^2 = CH_2CH_2OC_2H_5$, of melting point 109°–110° C.

| $C_{15}H_{16}O_4N_2S$ (320) | | | | |
|---|---|---|---|---|
| C | H | O | N | S |
| calculated 56.24 | 5.03 | 19.98 | 8.74 | 10.01 |
| found 56.3 | 5.0 | 19.6 | 8.9 | 10.1 |

EXAMPLE 10

2-Phenoxyethyl N-(4-phenyl-thiazol-2-yl)-oxamate

If in place of ethylene glycol monomethyl ether, 8.6 g of ethylene glycol monophenyl ether are used and in other respects the method of Example 7 is followed, crystallization of the product from ethyl alcohol/ethylene glycol monomethyl ether gives 5.6 g of the compound of the formula I, with $R^1 = C_6H_5$ and $R^2 = CH_2CH_2OC_6H_5$, of melting point 138°–140° C.

| $C_{19}H_{16}O_4N_2S$ (368) | | | | |
|---|---|---|---|---|
| C | H | O | N | S |
| calculated 61.94 | 4.38 | 17.37 | 7.60 | 8.70 |
| found 62.1 | 4.5 | 17.4 | 7.8 | 8.7 |

EXAMPLE 11

2-(ω-Methoxyethyleneoxy)-ethyl N-(4-phenyl-thiazol-2-yl)-oxamate

Using a method similar to Example 7, 6.2 g of N-(4-phenyl-thiazol-2-yl)-oxamic acid and 7.5 g of diethylene glycol monoethyl ether give, after crystallization of the product from isopropanol, 5.5 g of the compound of the formula I, with $R^1 = C_6H_5$ and $R^2 = CH_2CH_2OCH_2CH_2OCH_3$, of melting point 80°–81° C.

| $C_{16}H_{18}O_5N_2S$ (350) | | | | |
|---|---|---|---|---|
| C | H | O | N | S |
| calculated 54.85 | 5.18 | 22.83 | 7.99 | 9.15 |
| found 54.7 | 5.2 | 22.6 | 8.2 | 9.2 |

EXAMPLE 12

2-(ω-Ethoxyethyleneoxy)-ethyl N-(4-phenyl-thiazol-2-yl)-oxamate

A suspension of 6.2 g of N-(4-phenyl-thiazol-2-yl)-oxamic acid in 25 ml of dry toluene is refluxed for 2 hours with 20 ml of oxalyl chloride. After the excess oxalyl chloride has been distilled off, a mixture of 8.4 g of diethylene glycol monomethyl ether, 3.5 ml of triethylamine and 20 ml of toluene is added dropwise at room temperature. Stirring is continued for 18 hours at room temperature and the reaction product is then precipitated with naphtha. The precipitate is filtered off and stirred thoroughly with water. The residue is filtered off and dried, the dried material is taken up in warm ethyl acetate and the mixture is filtered. The filtrate is evaporated to dryness under reduced pressure and the residue is recrystallized from cyclohexane. 3.4 g of the compound of the formula I, with $R^1 = C_6H_5$ and $R^2 = CH_2CH_2OCH_2CH_2OC_2H_5$, of melting point 65°–68° C. are obtained.

| $C_{17}H_{20}O_5N_2S$ (364) | | | | |
|---|---|---|---|---|
| C | H | O | N | S |
| calculated 56.03 | 5.53 | 21.95 | 7.69 | 8.80 |
| found 56.0 | 5.4 | 21.2 | 8.0 | 9.1 |

EXAMPLE 13

2-Ethylthioethyl N-(4-phenyl-thiazol-2-yl)-oxamate

Using a method similar to Example 12, 6.2 g of N-(4-phenyl-thiazol-2-yl)-oxamic acid and 6.6 g of ethylthioethanol give, after crystallization of the product from ethanol, 3.4 g of the compound of the formula I, with $R^1 = C_6H_5$ and $R^2 = CH_2CH_2SC_2H_5$, of melting point 148°–149° C.

|  | $C_{15}H_{16}O_3N_2S_2$ (336) | | | | |
|---|---|---|---|---|---|
|  | C | H | O | N | S |
| calculated | 53.55 | 4.79 | 14.27 | 8.33 | 19.06 |
| found | 53.6 | 4.7 | 14.1 | 8.5 | 19.6 |

EXAMPLE 14

2-Ethoxyethyl N-[4-(4-methoxyphenyl)-thiazol-2-yl]-oxamate

Using a method similar to Example 12, 6.95 g of N-[4-(4-methoxyphenyl)-thiazol-2-yl]-oxamic acid and 5.6 g of ethylene glycol monoethyl ether give, after crystallization of the crude product from ethanol/active charcoal, 4 g of the compound of the formula I, with $R^1 = 4-OCH_3-C_6H_4$ and $R^2 = CH_2CH_2-OC_2H_5$, of melting point 130°–133° C.

|  | $C_{16}H_{18}O_5N_2S$ (350) | | | | |
|---|---|---|---|---|---|
|  | C | H | O | N | S |
| calculated | 54.84 | 5.17 | 22.83 | 7.99 | 9.15 |
| found | 54.8 | 5.1 | 23.0 | 8.2 | 9.0 |

EXAMPLE 15

2-Ethoxyethyl N-[4-(2,4,6-trimethylphenyl)-thiazol-2-yl]-oxamate

Using a method similar to Example 1, 10.9 g of 4-(2,4,6-trimethylphenyl)-2-aminothiazole and 9.9 g of 2-ethoxyethyl-oxalyl chloride give, after crystallization of the crude product from ethanol, 5 g of the above compound, of melting point 124°–125° C.

|  | $C_{18}H_{22}O_4N_2S$ (362) | | | | |
|---|---|---|---|---|---|
|  | C | H | O | N | S |
| calculated | 59.65 | 6.12 | 17.66 | 7.73 | 8.85 |
| found | 59.9 | 5.9 | 17.6 | 7.7 | 8.8 |

EXAMPLE 16

2-(ω-Ethoxyethyleneoxy)-ethyl N-[4-(2,4,6-trimethylphenyl)-thiazol-2-yl]-oxamate Using a method similar to Example 8, 10.9 g of 4-(2,4,6-trimethylphenyl)-2-aminothiazole and 12.5 g of 2-(ω-ethoxyethyleneoxy)-ethyl-oxalyl chloride give, after crystallization of the product from isopropanol, 13.4 g of the above compound, of melting point 114°–116° C.

|  | $C_{20}H_{26}O_5N_2S$ (407) | | | | |
|---|---|---|---|---|---|
|  | C | H | O | N | S |
| calculated | 59.09 | 6.45 | 19.68 | 6.89 | 7.89 |
| found | 59.0 | 6.4 | 19.9 | 7.1 | 7.8 |

EXAMPLE 17

2-Ethoxyethyl N-[4-(2,5-dimethoxyphenyl)-thiazol-2-yl]-oxamate

Using a method similar to Example 1, 11.8 g of 4-(2,5-dimethoxyphenyl)-2-aminothiazole and 9.9 g of 2-ethoxyethyl-oxalyl chloride give, after crystallization of the product from ethanol, 12.5 g of the above compound, of melting point 140°–141° C.

|  | $C_{17}H_{30}O_6N_2S$ (380) | | | | |
|---|---|---|---|---|---|
|  | C | H | O | N | S |
| calculated | 53.67 | 5.30 | 25.23 | 7.36 | 8.43 |
| found | 54.0 | 5.4 | 25.1 | 7.5 | 8.4 |

EXAMPLE 18

2-Ethoxyethyl N-[4-(2,4-dimethoxyphenyl)-thiazol-2-yl]-oxamate

Using a method similar to Example 1, 11.8 g of 4-(2,4-dimethoxyphenyl)-2-aminothiazole and 9.5 g of 2-ethoxyethyl-oxalyl chloride give, after digestion of the crude product with ether and crystallization from ethanol, 7 g of the above compound, of melting point 118°–120° C.

|  | $C_{17}H_{20}O_6N_2S$ (380) | | | | |
|---|---|---|---|---|---|
|  | C | H | O | N | S |
| calculated | 53.67 | 5.30 | 25.23 | 7.36 | 8.43 |
| found | 54.0 | 5.3 | 24.8 | 7.7 | 8.7 |

EXAMPLE 19

2-Ethoxyethyl N-[4-(4-ethoxyphenyl)-thiazol-2-yl]-oxamate

Using a method similar to Example 1, 11.0 g of 4-(4-ethoxyphenyl)-2-aminothiazole and 9.9 g of 2-ethoxyethyl-oxalyl chloride give, after crystallization of the product from ethanol, 9.4 g of the compound of the formula I, with $R^1 = 4-OCH_3-C_6H_4$ and $R^2 = CH_2CH_2OC_2H_5$, of melting point 139°–140° C.

|  | $C_{17}H_{20}O_5N_2S$ (364) | | | | |
|---|---|---|---|---|---|
|  | C | H | O | N | S |
| calculated | 56.03 | 5.53 | 21.95 | 7.69 | 8.80 |
| found | 56.3 | 5.7 | 21.7 | 7.7 | 8.8 |

EXAMPLE 20

2-Ethoxyethyl N-[4-(4-tert.-butylphenyl)-thiazol-2-yl]-oxamate

Using a method similar to Example 8, but with addition of 10 ml of dimethylformamide to the reaction mixture, 11.6 g of 4-(4-tert.-butylphenyl)-2-aminothiazole and 9.9 g of 2-ethoxyethyl-oxalyl chloride give, after crystallization of the product from isopropanol, 11.8 g of the compound of the formula I, with $R^1 = 4-C(CH_3)_3-C_6H_4$ and $R^2 = CH_2CH_2OC_2H_5$, of melting point 158°–160° C.

|  | $C_{19}H_{24}O_4N_2S$ (376) | | | | |
|---|---|---|---|---|---|
|  | C | H | O | N | S |
| calculated | 60.62 | 6.43 | 17.00 | 7.44 | 8.52 |
| found | 60.9 | 6.5 | 17.2 | 7.6 | 8.5 |

EXAMPLE 21

2-(ω-Ethoxyethyleneoxy)-ethyl N-[4-(2,4-dimethoxyphenyl)-thiazol-2-yl]-oxamate

Using a method similar to Example 8, 11.8 g of 4-[2,4-dimethoxyphenyl]-2-aminothiazole and 12.5 g of 2-(ω-ethoxyethyleneoxy)-ethyl-oxalyl chloride give, after crystallization of the product from isopropanol and treatment of the crystals with dilute aqueous triethylamine solution, 6 g of the above compound, of melting point 80°–82° C.

| | $C_{19}H_{24}O_7N_2S$ (424) | | | | |
|---|---|---|---|---|---|
| | C | H | O | N | S |
| calculated | 53.76 | 5.70 | 26.38 | 6.60 | 7.55 |
| found | 54.0 | 6.0 | 26.2 | 6.4 | 7.2 |

EXAMPLE 22

2-Propoxyethyl N-(4-phenyl-thiazol-2-yl)-oxamate

Using a method similar to Example 8, 8.8 g of 2-amino-4-phenylthiazole and 10.7 g of 2-propoxyethyloxalyl chloride give, after crystallization of the product from isopropanol/active charcoal, 5.9 g of the compound of the formula I, with $R^1 = C_6H_5$ and $R^2 = CH_2CH_2OC_3H_7$, of melting point 94°–96° C.

| | $C_{16}H_{18}O_4N_2S$ (334) | | | | |
|---|---|---|---|---|---|
| | C | H | O | N | S |
| calculated | 54.47 | 5.43 | 15.14 | 8.38 | 9.59 |
| found | 57.2 | 5.4 | 19.3 | 8.5 | 9.5 |

EXAMPLE 23

2-Butoxyethyl N-(4-phenyl-thiazol-2-yl)-oxamate 8.8 g of 2-amino-4-phenylthiazole are reacted with 11.4 g of 2-butoxyethyl-oxalyl chloride by a method similar to Example 8. The crude product is purified as follows: it is crystallized from cyclohexane, the crystals are dissolved in chloroform and the solution is treated with active charcoal, and the residue which remains after concentrating the chloroform filtrate is treated with petroleum ether and finally with dilute sodium bicarbonate solution. 4.3 g of the compound of the formula I, with $R^1 = C_6H_5$ and $R^2 = CH_2CH_2OC_4H_9$, of melting point 94°–95° C. are obtained.

| | $C_{17}H_{20}O_4N_2S$ (348) | | | | |
|---|---|---|---|---|---|
| | C | H | O | N | S |
| calculated | 58.60 | 5.79 | 18.37 | 8.04 | 9.20 |
| found | 58.6 | 5.9 | 18.4 | 8.3 | 9.3 |

Examples of pharmaceutical formulations:

Tablets

| (a) | Active compound of the invention | 0.100 g |
|---|---|---|
| | Stearic acid | 0.010 g |
| | Glucose | 1.890 g |
| | | 2.000 g |
| (b) | Active compound of the invention | 0.020 g |
| | Stearic acid | 0.020 g |
| | Glucose | 1.960 g |

—continued

| | 2.000 g |
|---|---|

The constituents are converted to tablets, having the above composition, in a conventional manner.

Inhalation aerosol

| Active compound | 1.00 part |
|---|---|
| Soybean lecithin | 0.20 part |
| Propellent gas mixture | |
| (Frigen 11, 12 and 114) to make up to | 100.00 parts |

The formulation is preferably packaged in aerosol containers having a dosing valve, and so arranged that a single operation dispenses a dose of 5–20 mg of active compound.

Ampoules (injection solutions)

| Active compound | 50.0 parts by weight |
|---|---|
| Sodium pyrosulfite | 1.0 part by weight |
| Disodium ethylenediaminetetra-acetate | 0.5 part by weight |
| Sodium chloride | 8.5 parts by weight |
| Doubly distilled water to make up to | 1,000.0 parts by weight |

The active compound and the auxiliaries are dissolved in a sufficient amount of water and brought to the desired concentration with the required amount of water. The solution is filtered and filled into 1 ml ampoules under aseptic conditions. Finally, the ampoules are sterilized and sealed.

We claim:

1. A compound of formula I

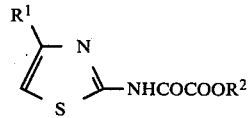

where $R^1$ is phenyl which is unsubstituted or in monosubstituted or disubstituted by hydroxyl, or is monosubstituted, disubstituted or trisubstituted by methoxy or ethoxy, or is monosubstituted by methylenedioxy or ethylenedioxy and $R^2$ is a radical of the formula $-(CH_2CH_2O)_m-CH_2CH_2OR^3$, $-(CHR^4-CHR^5O)_n-CHR^4-CHR^5OR^3$ or $-CH_2CH_2-SR^6$ where m and n are each an integer from 0 to 3, $R^3$ is hydrogen or an alkyl of 1 to 4 carbon atoms, $R^4$ and $R^5$ are each hydrogen or methyl and $R^6$ is an alkyl of 1 to 4 carbon atoms.

2. A compound of the formula I according to claim 1, where $R^1$ is phenyl which is unsubstituted or substituted by methoxy and $R^2$ is a radical of the formula $-(CH_2CH_2O)_m-CH_2CH_2OR^3$, where m is 0 or 1 and $R^3$ is alkyl of 1 to 4 carbon atoms.

3. 2-Ethoxyethyl N-(4-phenyl-thiazol-2-yl)-oxamate.

4. 2-Methoxyethyl N-(4-phenyl-thiazol-2-yl)-oxamate.

5. 2-(ω-Methoxyethyleneoxy)-ethyl N-(4-phenyl-thiazole-2-yl)-oxamate.

6. 2-Ethoxyethyl N-[4-(4-methoxyphenyl)-thiazol-2-yl]-oxamate.

7. A therapeutic agent for the treatment of allergic disorders which contains an effective amount of a compound of the formula I as claimed in claim 1 as the active compound, together with conventional carriers and diluents.

8. A therapeutic agent as described in claim 7 wherein the active compound is selected from the group consisting of 2-ethoxyethyl N-(4-phenyl-thiazol-2-yl)-oxamate, 2-methoxyl N-(phenyl-thiazol-2-yl)-oxamate, 2-(ω-methoxyethyleneoxy)-ethyl N-(4-phenyl-thiazole-2-yl)-oxamate, and 2-ethoxyethyl N-[4-(4-methoxyphenyl)-thiazol-2-yl]-oxamate.

* * * * *